(12) United States Patent
Bublewitz et al.

(10) Patent No.: US 7,858,673 B2
(45) Date of Patent: Dec. 28, 2010

(54) METHOD FOR STERILIZING IMPRESSION MATERIALS AND IMPRESSION MATERIAL THAT CAN BE STERILIZED

(75) Inventors: Alexander Bublewitz, Herborn (DE); Jens-Peter Reber, Meinerzhagen (DE); Matthias Suchan, Hachenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 159 days.

(21) Appl. No.: 11/803,202

(22) Filed: May 14, 2007

(65) Prior Publication Data

US 2007/0261986 A1 Nov. 15, 2007

(30) Foreign Application Priority Data

May 15, 2006 (DE) .................. 10 2006 022 880

(51) Int. Cl.
*A61K 6/10* (2006.01)
(52) U.S. Cl. ..................... 523/109; 422/25; 422/28
(58) Field of Classification Search ........... 422/28, 422/25, 26, 27; 523/109
See application file for complete search history.

(56) References Cited

U.S. PATENT DOCUMENTS

| 6,299,022 | B1 | 10/2001 | Bublewitz et al. |
|---|---|---|---|
| 6,352,177 | B1 | 3/2002 | Bublewitz et al. |
| 6,394,643 | B1 | 5/2002 | Bublewitz et al. |
| 6,599,974 | B1 * | 7/2003 | Bublewitz et al. ........... 524/588 |
| 6,644,509 | B1 | 11/2003 | Bublewitz et al. |
| 2004/0009093 | A1 | 1/2004 | Grunwald et al. |
| 2004/0084812 | A1 | 5/2004 | Grunwald et al. |
| 2004/0229971 | A1 | 11/2004 | Rossi et al. |
| 2005/0159522 | A1 | 7/2005 | Bublewitz et al. |
| 2006/0281856 | A1 * | 12/2006 | Kollefrath et al. ........... 524/588 |

FOREIGN PATENT DOCUMENTS

| DE | 103 29 359 A1 | 10/2004 |
|---|---|---|
| EP | 0 579 132 | 7/1993 |
| EP | 1 065 153 B1 | 1/2001 |
| EP | 1 112 779 B1 | 7/2001 |
| EP | 1 121 195 B1 | 8/2001 |
| EP | 1 138 397 B1 | 10/2001 |
| EP | 1 169 242 B1 | 1/2002 |
| EP | 1 347 914 A1 | 1/2004 |
| EP | 1 347 915 A1 | 1/2004 |
| EP | 1 477 151 A1 | 11/2004 |
| WO | WO 95/11706 | 5/1995 |
| WO | WO 01/89588 | 11/2001 |
| WO | WO 02/088252 | 11/2002 |
| WO | WO 2004/052994 A1 | 6/2004 |

* cited by examiner

*Primary Examiner*—Sean E Conley
(74) *Attorney, Agent, or Firm*—Collard & Roe, P.C.

(57) ABSTRACT

A method for sterilizing medical single-component or multi-component impression materials that can harden, and a two-component impression material. In a first step of the method, the components of the impression materials that have not hardened are introduced into a primary packaging. In a second step, the primary packagings, with the components contained therein, are sterilized by heat sterilization. In a third step, the sterilized components in the primary packagings are introduced into a secondary packaging. In a fourth step, this secondary packaging is sterilized by means of a suitable gas sterilization, irradiation sterilization, and/or by means of sterilization in an autoclave, so that the activity and the viscosity of the components are not changed.

25 Claims, 1 Drawing Sheet

Fig. 1a    Fig. 1b    Fig. 1c    Fig. 1d
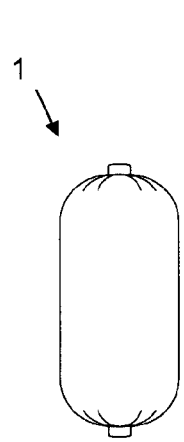
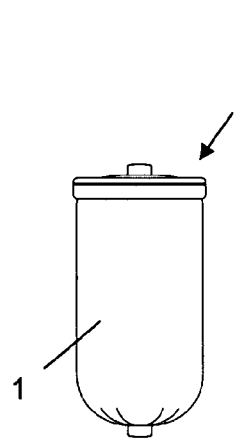
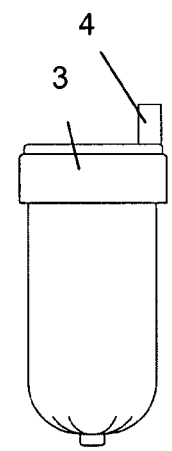
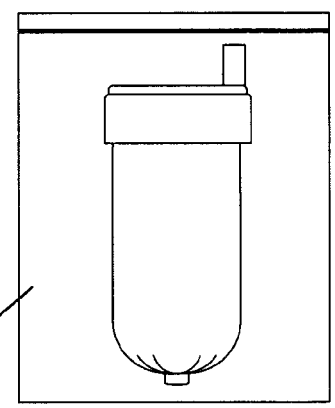
Fig. 2a    Fig. 2b    Fig. 2c
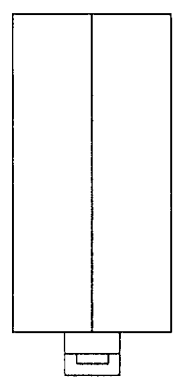
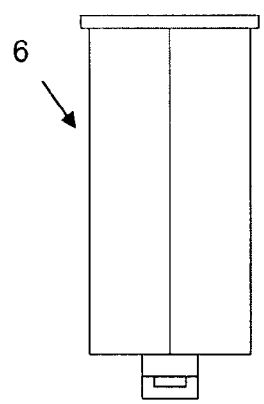
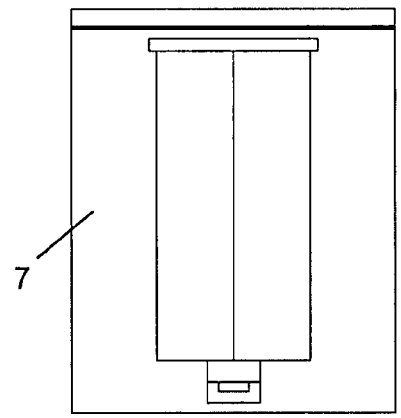
Fig. 3a    Fig. 3b
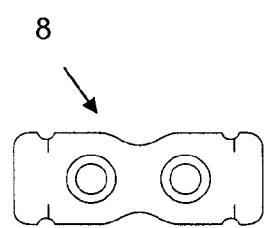
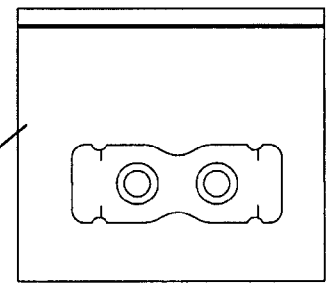

METHOD FOR STERILIZING IMPRESSION MATERIALS AND IMPRESSION MATERIAL THAT CAN BE STERILIZED

BACKGROUND OF THE INVENTION

1. Field of the Invention

The present invention relates to a method, particularly a multi-stage method, for sterilizing medical single-component or multi-component impression materials that can harden. Furthermore, the invention relates to an impression material that can be sterilized.

2. The Prior Art

Impression materials are used in great numbers and vary greatly in the number of components, the combinations of the individual components, or the method of curing.

Thus, for example, systems are used that cure by means of an addition reaction, such as addition-cross-linking silicone molding materials or corresponding polyether impression materials. Alternatively, condensation-cross-linking systems are used; condensation-cross-linking silicone and polyether impression materials will be mentioned as examples here.

Predominantly, these materials are used in two-component systems, which cure, i.e. harden after being mixed, in a more or less short period of time.

In medical uses, however, the problem often occurs that the material, which is in paste form initially, comes into contact with skin injuries or mucous membrane injuries or surgically exposed structures, in the mouth, or in endoprosthetics, in the case of hip joint prostheses or knee joint prostheses, whereby there is the risk that bacteria, fungi, or viruses will be transferred. This can lead to significant health impairments. Furthermore, the use of a sterile material that can harden can be necessary in dental medicine, for example as a root filler material.

Similar problems can also occur if the material as such is kept germ-free, but the objects used for its use, such as impression trays, mixers, or cartridge bodies, are not sterile and therefore carry germs.

For this reason, there is great interest in a sterile impression material and in sterile equipment for its application.

European Patent No. EP 1 477 151 A1 describes a sterilization method in which sterilization takes place by boiling at 100° C., or autoclaving takes place at 121° C. Also, sterilization with gamma rays, as well as the use of electron beams and X-rays, is proposed, but this can damage the impression material.

In European Patent No. EP 1 374 914 A1, a method is presented in which impression materials and/or their components are subjected to steam sterilization. In this connection, tins, tubular bags, tubes, syringes, and dual-chamber cartridges are used as so-called primary packaging, in which the components are contained. These are introduced into a sterilization packaging, together with accessories needed for application of the impression masses, such as mixing dies. This packaging with contents is then subjected to steam sterilization. In this connection, the temperature to be set amounts to preferably at most 138° C., according to European Patent No. EP 1 374 914 A1, and the duration of the method amounts to at most 30 minutes. According to EP 1 374 914 A1, the material can suffer irreparable damage due to longer reaction times and higher temperatures.

Another disadvantage of this method, i.e. the simultaneous sterilization of all of the components, in other words the masses to be cross-linked and the equipment used for this purpose, is that only conditions that can be tolerated by all the parts, with regard to their stability, can be applied. Parts that cannot be steam-sterilized, such as polyethylene closure caps, for example, otherwise suffer irreparable damage.

A similar concept is pursued by European Patent No. EP 1 374 915 A1. Here, the sterilization step takes place by irradiation sterilization. However, it is disadvantageous in this connection that addition-cross-linking silicone impression materials, in particular, already pre-cross-link at higher radiation doses, and therefore are no longer usable for any subsequent use for their intended purpose.

SUMMARY OF THE INVENTION

It is therefore an object of the present invention to make available a method for sterilizing medical single-component or multi-component impression materials that can harden, in which both the single-component or multi-component material and its surrounding packaging (primary packaging) and, if applicable, also any equipment used for the application, are reliably sterilized, without the occurrence of any prior damage, particularly pre-cross-linking, reduced storage stability, changes in viscosity, or changes in reactivity of the single-component or multi-component material or damage to the equipment.

This object is accomplished according to the invention by a method having the following steps: Packaging of the components, individually or jointly, in at least one heat-resistant packaging, wherein at least one of the packagings is gas-tight, and subsequent sterilization of the components by heat, preferably dry heat, at a temperature greater than 138° C., and at approximately normal pressure. Sterilization at the high temperature greater than 138° C., according to the invention, has the advantage that not only outer regions of a component, for example one accommodated in a tubular bag or a cartridge, but also its core will be sufficiently heated to sterilize the component. In this connection, the gas-tight packaging prevents oxidation of the components with the ambient air. Different packagings can be used for the method according to the invention. For example, the components can be accommodated directly in a heat-stable cartridge, which is as gas-impermeable as possible, which is fluorinated and has openings closed off with an aluminum laminate foil. Alternatively to this, it is also possible to accommodate the components in a tubular bag or another suitable bag made of a metal laminate foil.

In the method according to the invention, the components can be accommodated, during sterilization with dry heat, either in a gas-tight primary packaging with no secondary packaging, or a gas-tight or gas-permeable secondary packaging can be provided, or the components are either accommodated, during sterilization with dry heat, in a primary packaging that is not gas-tight, whereby then, a gas-tight secondary packaging is provided.

According to a preferred embodiment of the method according to the invention, ambient air is preferably removed almost completely from the packaging before the packaging is sealed in a gas-tight manner, and/or the packaging is filled with inert gas. In this way, an oxidation reaction of the components, which could make these unusable, is avoided in a particularly effective manner. The residual air can be is forced out of the packaging to a great extent, by way of a soft punch, for example a foam rubber punch, so that only small residual amounts of air, if any, remain in the packaging. However, it is preferred if the residual air is drawn out of the packaging at least almost completely and/or the packaging is filled with inert gas.

A particularly preferred embodiment of the invention provides that in a first step, the components of the medical impression materials that have not hardened are each introduced into a primary packaging. In a second step, the primary packagings, with the components contained therein, are sterilized by heat sterilization, particularly by dry heat. In a third step, the sterilized components in the primary packagings are introduced into a secondary packaging. In a fourth step, this secondary packaging is sterilized by means of a suitable gas sterilization, i.e., one that is appropriate in terms of concentration and duration, and/or by means of a suitable irradiation sterilization, i.e. an irradiation sterilization at a radiation dose that is high enough to sterilize the surfaces of the primary packaging and the additionally provided equipment, if applicable, and, at the same time, is low enough so that the impression material is not damaged, and/or by means of sterilization in an autoclave that is suitable in terms of duration, pressure, and temperature, in such a manner that the activity and the viscosity of the components are not changed. This is understood to mean that the activity of the components changes so little that the hardening time does not lengthen or shorten by more or less than one minute, and/or that the change in viscosity of the components amounts to less than approximately 20%, preferably less than 10%, very particularly preferably less than 5%. As an alternative to heat sterilization by dry heat, the primary packaging can also be sterilized by (water) steam or by boiling in the second step.

The first sterilization step is heat sterilization at a temperature that is suitable for the material. In contrast to sterilization by high-energy gamma radiation, no prior damage or pre-cross-linking of the impression material takes place in this connection.

The primary packagings are preferably selected in such a manner that they are not damaged during heat sterilization. The following high-temperature-resistant plastics, for example, are suitable for the primary packaging: cyclo-olefinic copolymers (e.g. Topas® 6015, Ticona), (co-)polycarbonates (e.g. APEC® 1745, Bayer), or polysulfone (e.g. Ultrason® S 3010, BASF). Furthermore, plastic/metal/plastic laminate packagings, particularly foil packs or blister packs, metal tubes or metal laminate tubes, metal laminate foil tubular bags, metal cartridges or metal laminate cartridges, particularly polypropylene/aluminum/polypropylene laminate packagings, aluminum tubes, tin tubes, aluminum/tin laminate tubes, aluminum cartridges, tin cartridges, or aluminum/tin laminate cartridges, are particularly suitable. In this connection, the metal cartridges, metal tubes, metal foils and/or blisters can also have internal coatings. The plastic primary packagings used can also be fluoridated. These materials can also be exposed to higher temperatures than conventional polyethylene outside packagings, for example.

In a preferred embodiment, the primary packaging is provided with an activation head or introduced into a cartridge and closed off with a piston. Such combinations, for example of a primary packaging configured as a foil bag packaging, with components of a system for mixing and/or dispensing the components accommodated in the primary packaging, are described, for example, in European Patent Nos. EP 1 065 153, EP 1 169 242, EP 1 138 397, EP 1 112 779, as well as in EP 1 121 195.

In addition to the usual heat sterilization methods, dry heat sterilization preferably takes place at a temperature T greater than 138° C. and less than or equal to 160° C., preferably at a temperature T greater than or equal to 140° C. and less than or equal to 150° C., and particularly preferably at a temperature T greater than or equal to 140° C. and less than or equal to 145° C.

In this connection, in the case of heat sterilization, a treatment time greater than or equal to one hour is preferably selected, particularly preferably a time of greater than or equal to 1.5 hours, and very particularly preferably, a time of greater than 2 hours once the core temperature has been reached.

By means of this selection of the parameters of temperature and treatment time, it is guaranteed that the germ reduction in the treated material is optimal, and that the sterilized material can be used without reservations for the intended medical purposes.

In a second step, the sterilized primary packagings are introduced into a secondary packaging, and this combination is subjected to a second sterilization. This sterilizes the outside of the primary packagings, which can become contaminated during further processing, for example during processing for final packaging.

Any known form of packaging that can be sealed and withstands the conditions of the second sterilization can serve as secondary packaging. In a particularly preferred embodiment, the secondary packaging is a plastic bag or sterile bag that can be transparent, opaque and/or imprinted. Preferably, the secondary packaging is also temperature-resistant. It can consist, for example, of one of the following high-temperature-resistant plastics: cyclo-olefinic copolymers (e.g. Topas® 6015, Ticona), (co-)polycarbonates (e.g. APEC® 1745, Bayer), or polysulfone (e.g. Ultrason® S 3010, BASF).

The second sterilization is a suitable gas sterilization, irradiation sterilization and/or sterilization in an autoclave, for example. In the case of gas sterilization, sterilization with ethylene oxide (EO, Oxiran), for example, is preferred. Irradiation sterilization is preferably a suitable sterilization with a-rays, b-rays, or X-rays.

The treatment time in this second step can be significantly less than that of the first sterilization step. In this connection, a treatment time of less than or equal to one hour, particularly less than or equal to 30 minutes, and particularly preferably less than or equal to 10 minutes is preferred. In this way, the possibility of damage to the materials, particularly of the impression materials, is prevented, for one thing, and for a second thing, an acceptable total duration of the sterilization process is achieved, with simultaneous sufficient sterilization quality.

In total, a sterile material is obtained by means of this method, in which the components do not become unusable due to pre-cross-linking, and/or the catalyst is damaged, and which is stable in storage for a sufficiently long time after sterilization, for example for 24 months.

Preferably, the accessories needed for application of the impression mass, such as a dynamic or static mixer, impression tray, activation heads, cartridges and/or cartridge bodies, are also introduced into the secondary packaging. Because the second sterilization is shorter and gentler with regard to temperature, in comparison with heat sterilization, than that applied during the first step, these accessories do not suffer any damage, even if they are not produced from heat-resistant material.

According to an advantageous embodiment of the invention, the components of the single-component or multi-component impression material are filled into an appropriate number of tubular bags, which are capped with a sealing ring and an activation head after sterilization by dry heat. Subsequently, the tubular bags with sealing ring and activation head are packaged into a sterile bag and sealed, and this bag is sterilized by a suitable ethylene oxide sterilization and/or suitable a-ray, b-ray, and/or X-ray sterilization, and/or suitable sterilization in an autoclave. It is also possible to package the capped sterilized tubular bags and individual or several accessories in a common sterile bag, so that these are jointly subjected to ethylene oxide sterilization and/or a suitable a-ray, b-ray, and/or X-ray sterilization and/or sterilization in an autoclave.

According to another embodiment of the invention, the components sterilized by dry heat in tubular bags that can have a content of approximately 1 ml to approximately 400 ml, for example, are introduced into a suitable cartridge and sealed. The cartridges, which preferably accommodate two tubular bags, as double cartridges, are then packaged in sterile bags and sealed, individually or together with accessories, such as one or more static mixers and/or a dispensing gun, for example. Depending on the type of packaging, the cartridges and accessories can therefore be sterilized individually or jointly, by means of suitable ethylene oxide sterilization and/or suitable a-ray, b-ray, and/or X-ray sterilization and/or sterilization in an autoclave.

According to another preferred embodiment of the invention, the components can be filled into a plastic, metal, or metal-coated cartridge that is suitable for sterilization and can be filled directly, particularly a double cartridge, which is then sealed and subjected to sterilization by heat. The cartridge sterilized in such a manner, with the components, is subsequently packaged into a sterile bag, alone or together with accessories, such as one or more static mixers and/or a dispensing gun, for example. Thus, the cartridge can be sterilized individually or jointly with accessories, by means of suitable ethylene oxide sterilization and/or suitable a-ray, b-ray, and/or X-ray sterilization and/or sterilization in an autoclave.

If the components are filled into a blister pack that can be filled directly, as a primary packaging, this is subjected to sterilization by dry heat, according to another embodiment of the invention, after being sealed. The sterilized blister pack with the components is packaged into a sterile bag, together with mixing accessories, such as a spatula or the like, which bag is sterilized by suitable ethylene oxide sterilization and/or suitable a-ray, b-ray, and/or X-ray sterilization and/or sterilization in an autoclave. Alternatively to this, it is also possible, according to the invention, to package the blister pack and accessories in separate sterile bags and sterilize them by suitable ethylene oxide sterilization and/or suitable a-ray, b-ray, and/or X-ray sterilization and/or sterilization in an autoclave.

Gas sterilization can also be achieved, alternatively or in addition to the method indicated above (introduction of the materials intended for the second sterilization step into a sterile packaging, closing of the packaging, and subsequent sterilization by means of a gas that penetrates into the packaging), in that the sterilizing gas is introduced into the sterile package together with the materials to be sterilized, before the package is sealed.

According to a preferred embodiment, the medical impression material that can harden is based on polysiloxanes, alkoxy-functional polyethers, aziridino-functional polyethers, or acrylate-functional and/or methacrylate-functional polyethers.

In a particularly preferred embodiment, the impression material is a two-component impression material, particularly an addition-cross-linking two-component silicone impression material.

According to the invention, an addition-cross-linking two-component silicone material is particularly suitable for a method of the type mentioned above, as a medical impression material, which contains, in the first component A,
 a) at least one hydrosilylation catalyst,
 b) at least one vinyl end-stopped polydialkyl siloxane, and
 c) at least 0.001 up to particularly approximately 1 wt.-% of at least one stabilizer, particularly preferably 0.005 to 0.5 wt-% of at least one stabilizer, and very particularly preferably 0.01 to 0.1 wt.-% of at least one stabilizer, particularly a divinyl disiloxane, hydroxyanisol, butyl hydroxytoluene, divinyl hexamethyl trisiloxane, phenothiazine, phosphite and/or HALS (hindered amine light stabilizer), and in the second component B
 d) at least one organohydrogen polysiloxane.

The at least one stabilizer and the at least one hydrosilylation catalyst, for example a platinum divinyl disiloxane complex, particularly a platinum divinyl tetramethyl disiloxane complex, are coordinated with one another in such a manner that during sterilization using the method indicated above, no noteworthy pre-cross-linking takes place, so that the activity of the hydrosilylation catalyst, i.e. the ability of the vinyl and SiH groups to cross-link, essentially does not change. In other words, the hardening time does not lengthen or shorten by more or less than one minute. Furthermore, the change in viscosity of the individual components A and B amounts to less than approximately 20%, preferably less than 10%, very particularly preferably less than 5%. The components, particularly the catalyst, are therefore not damaged by the sterilization or made unusable by means of pre-cross-linking, so that the impression material according to the invention remains stable in storage for a sufficiently long time, particularly for at least approximately 24 months.

In addition, the component A can contain
 e) at least one non-functional polymer and/or
 f) mineral oils and/or waxes and/or
 g) at least one substance having an anti-bacterial/anti-microbial effect and/or
 h) at least one substance opaque to X-rays and/or
 i) reinforcing and/or non-reinforcing fillers and/or
 j) pigments and/or
 k) additives and/or
 l) surfactants and/or the component B can contain
 b) at least one end-stopped vinyl polydialkyl siloxane and/or
 e) at least one non-functional polymer and/or
 f) mineral oils and/or waxes and/or
 g) at least one substance having an anti-bacterial/anti-microbial effect and/or
 h) at least one substance opaque to X-rays and/or
 i) reinforcing and/or non-reinforcing fillers and/or
 k) additives and/or
 l) surfactants.

According to a preferred embodiment, the non-functional polymer d) is a trimethyl siloxy end-stopped polydialkyl siloxane and/or the substance g) having an anti-bacterial/anti-microbial effect is selected from the group consisting of micro-silver, nano-silver, (micro-/nano-) copper oxide, (micro-/nano-) zinc oxide).

Another object of the invention is a kit consisting of at least one primary packaging that is filled with a component of a multi-component impression material and of at least one accessory, particularly at least one dynamic or static mixer, at least one impression tray, at least one spatula or similar mixing accessory, at least one activation head, at least one sealing ring, at least one cartridge and/or at least one dispensing gun or similar dispensing device. At least the primary packaging with the component is sterilized according to a method according to the invention. Preferably, the at least one accessory is also sterilized.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIGS. 1a-1d show the method steps during sterilization of a tubular bag, according to the invention;

FIGS. 2a-2c show the method steps during sterilization of a directly filled cartridge, according to the invention; and FIGS. 3a-3b show the method steps during sterilization of a blister pack, according to the invention.

DETAILED DESCRIPTION OF THE PREFERRED EMBODIMENT

According to the embodiment of the invention shown in FIGS. 1a to 1d, a component of a single-component or multi-component impression material is filled into a tubular bag 1, which can have a content of approximately 1 ml to approximately 400 ml, for example. In tubular bag 1, the component is subjected to sterilization by dry heat, at a temperature of approximately 138° C. to approximately 150° C.

As shown in FIGS. 1b and 1c, the sterilized tubular bag 1 is then first capped with a sealing ring 2, which is glued onto tubular bag 1, for example. Furthermore, a cap-like activation head 3 is set onto sealing ring 2, which can engage with sealing ring 2. Activation head 3 is provided with an outlet nozzle 4, which can be connected with a mixer or the like, for dispensing the component accommodated in tubular bag 1.

Subsequently, tubular bag 1 with sealing ring 2 and activation head 3 is packaged into a sterile bag 5 shown in FIG. 1d, and sealed. Sterile bag 5 is subsequently sterilized by a suitable ethylene oxide sterilization and/or suitable a-ray, b-ray, and/or X-ray sterilization, and/or suitable sterilization in an autoclave.

Likewise, accessories not shown in the figures, such as dynamic or static mixers and/or reusable cartridge bodies, can be individually or jointly packaged in sterile bags and sealed, and also be sterilized. It is also possible to package the capped sterilized tubular bags and individual or several accessories in a common sterile bag, so that these are jointly subjected to sterilization.

According to another preferred embodiment of the invention, the components can be filled into a plastic, metal, or metal-coated cartridge that can be filled directly and is suitable for sterilization, particularly into a double cartridge 6 shown in FIG. 2a. Double cartridge 6 has closed outlet openings on the lower side in FIG. 2a, which can be connected with a mixer, not shown.

As shown in FIG. 2b, double cartridge 6 is also closed off on the side lying opposite the outlet openings after it has been filled, and then subjected to sterilization by dry heat. The cartridge sterilized in this manner, with the components, is subsequently packaged into a sterile bag 7 shown in FIG. 2c, alone or together with accessories such as one or more static mixers and/or a dispensing gun, for example. Thus, the double cartridge 6 can be sterilized by a suitable ethylene oxide sterilization and/or suitable a-ray, b-ray, and/or X-ray sterilization, and/or suitable sterilization in an autoclave.

When the components have been filled into a blister pack 8 that can be filled directly, as the primary packaging, as shown in FIG. 3a, this pack is subjected to sterilization by dry heat after it has been closed. Sterilized blister pack 8 with the components is packaged into a sterile bag 9 shown in FIG. 3b, if applicable with mixing accessories, not shown, such as a spatula or the like, which bag is sterilized by a suitable ethylene oxide sterilization and/or suitable a-ray, b-ray, and/or X-ray sterilization, and/or suitable sterilization in an autoclave.

Accordingly, while only a few embodiments of the present invention have been shown and described, it is obvious that many changes and modifications may be made thereunto without departing from the spirit and scope of the invention.

What is claimed is:

1. A two-component silicone material comprising:
   a first component A comprising:
   a) at least one hydrosilylation catalyst;
   b) at least one vinyl end-stopped polydialkyl siloxane; and
   c) between 0.001 and approximately 1 wt.-%, of at least one stabilizer; and
   a second component B comprising:
   d) at least one organohydrogen polysiloxane;
   wherein the at least one stabilizer and the at least one hydrosilylation catalyst are coordinated with one another so that during sterilization of the silicone material, activity of the hydrosilylation catalyst and viscosity of the individual components A and B does not change.

2. A method for sterilizing the two-component silicone material of claim 1 having the following steps:
   packaging each component, individually or jointly, in at least one heat-resistant packaging, at least one of said at least one packaging being gas-tight, and
   sterilizing the components with heat, at a temperature greater than 138° C., and at normal pressure, subsequent to said step of packaging.

3. The method according to claim 2, wherein before the at least one packaging is sealed gas-tight, ambient air is removed almost completely from the packaging, or the packaging is filled with inert gas.

4. A method for sterilizing the two-component silicone material of claim 1 having the following steps:
   introducing components of the impression materials that have not hardened into a primary packaging;
   sterilizing the primary packaging, with the components contained therein, by heat sterilization;
   introducing the sterilized components in the primary packaging into a secondary packaging; and
   sterilizing the secondary packaging by gas sterilization, irradiation sterilization, or by sterilization in an autoclave, in such a manner that activity and viscosity of the components are not changed.

5. The method according to claim 4, wherein the primary packaging is a plastic/metal/plastic laminate packaging.

6. The method according to claim 5, wherein the primary packaging is selected from the group consisting of: a polypropylene/aluminum/polypropylene laminate packaging, aluminum tube, tin tube, aluminum/tin laminate tube, aluminum cartridge, tin cartridge and aluminum/tin laminate cartridge.

7. The method according to claim 4, wherein the primary packaging is a metal cartridge, metal tube, metal foil or blister pack provided with at least one internal coating, or is a fluoridated plastic packaging.

8. The method according to claim 2, wherein the heat sterilization takes place at a temperature T greater than 138° C. and less than or equal to 160° C.

9. The method according to claim 2, wherein during heat sterilization, a treatment time greater than or equal to one hour is selected.

10. The method according to claim 4, wherein the secondary packaging is a plastic bag.

11. The method according to claim 4, wherein step of sterilizing the secondary packaging takes place by an ethylene oxide sterilization or a sterilization with a-rays, b-rays, or X-rays.

12. The method according to claim 4, wherein the secondary packaging is sterilized with a treatment time of less than or equal to one hour.

13. The method according to claim 4, further comprising the step of introducing at least one accessory into the secondary packaging, prior to said step of sterilizing the secondary packaging.

14. The method according to claim 13, wherein the at least one accessory is at least one dynamic or static mixer, at least one impression tray, at least one spatula or mixing accessory, at least one activation head, at least one sealing ring, at least one cartridge or at least one dispensing gun or dispensing device.

15. The method according to claim 2, wherein the single-component or multi-component impression material is selected from the group consisting of polysiloxanes, alkoxy-functional polyethers, aziridino-functional polyethers, acrylate-functional polyethers and methacrylate-functional polyethers.

16. The method according to claim 2, wherein the single-component or multi-component impression material is an addition-cross-linking two-component silicone impression material.

17. The method according to claim 4, wherein the step of sterilizing the secondary packaging comprises heat sterilization that takes place at a temperature T of less than 138° C., at normal pressure.

18. A two-component silicone impression material according to claim 1, further comprising at least one additive in at least one of component A and component B, said additive being selected from the following:
   in component A:
   e) at least one non-functional polymer;
   f) mineral oils or waxes;
   g) at least one substance having an anti-bacterial/anti-microbial effect;
   h) at least one substance opaque to X-rays;
   i) reinforcing or non-reinforcing fillers;
   j) pigments;
   k) additives; and
   l) surfactants; and
   in component B:
   b) at least one end-stopped vinyl polydialkyl siloxane;
   e) at least one non-functional polymer;
   f) mineral oils or waxes;
   g) at least one substance having an anti-bacterial/anti-microbial effect;
   h) at least one substance opaque to X-rays;
   i) reinforcing or non-reinforcing fillers;
   k) additives; and
   l) surfactants.

19. A two-component silicone impression material according to claim 1, wherein the at least one stabilizer is a divinyl disiloxane, hydroxyanisol, butyl hydroxytoluene, divinyl hexamethyl trisiloxane, phenothiazine, phosphite or HALS (hindered amine light stabilizer).

20. A two-component silicone impression material according to claim 19, wherein the hydrosilylation catalyst is a platinum divinyl disiloxane complex.

21. A two-component silicone impression material according to claim 18, wherein the additive is a substance having an anti-bacterial/anti-microbial effect and is selected from the group consisting of micro-silver, nano-silver, (micro-copper oxide, nano-copper oxide, micro-zinc oxide and nano-zinc oxide.

22. A kit comprising at least one primary packaging that is filled with at least one component of a multi-component impression material, and at least one accessory, wherein at least the primary packaging with the at least one component was sterilized by packaging the components, individually or jointly, in the primary packaging, and sterilizing the at least one component with dry heat, at a temperature greater than 138° C., and at standard atmosphere pressure, with the viscosity of the at least one sterilized component of the multi-component impression material being changed less than 20% compared with said component prior to its sterilization of said component.

23. A kit according to claim 22, wherein the at least one accessory was also sterilized.

24. A kit comprising at least one primary packaging that is filled with at least two components of a multi-component impression material, and at least one accessory, wherein at least the primary packaging with the at least two components was sterilized by packaging the components, individually or jointly, in the primary packaging, and sterilizing the at least two components with dry heat, at a temperature greater than 138° C., and at standard atmosphere pressure, with the viscosity of the at least two sterilized components of the multi-component impression material being changed less than 20% compared with said components prior to sterilization of said components.

25. A kit according to claim 24, wherein the at least one accessory was also sterilized.

* * * * *

UNITED STATES PATENT AND TRADEMARK OFFICE
CERTIFICATE OF CORRECTION

| | | |
|---|---|---|
| PATENT NO. | : 7,858,673 B2 | Page 1 of 1 |
| APPLICATION NO. | : 11/803202 | |
| DATED | : December 28, 2010 | |
| INVENTOR(S) | : Bublewitz et al. | |

It is certified that error appears in the above-identified patent and that said Letters Patent is hereby corrected as shown below:

Column 10, line 32 (Claim 22) after the word "to", please delete the word: "its".

Signed and Sealed this
Twelfth Day of April, 2011

David J. Kappos
*Director of the United States Patent and Trademark Office*